United States Patent
Hallek et al.

(10) Patent No.: US 7,314,912 B1
(45) Date of Patent: Jan. 1, 2008

(54) AAV SCLEROPROTEIN, PRODUCTION AND USE THEREOF

(75) Inventors: Michael Hallek, Schondorf (DE); Martin Ried, Sinning (DE); Gilbert Deleage, Lyons (FR); Anne Girod, München (DE)

(73) Assignee: Medigene Aktiengesellschaft, Planegg/Martinsried (DE)

( * ) Notice: Subject to any disclaimer, the term of this patent is extended or adjusted under 35 U.S.C. 154(b) by 0 days.

(21) Appl. No.: 09/720,066

(22) PCT Filed: Jun. 21, 1999

(86) PCT No.: PCT/EP99/04288

§ 371 (c)(1),
(2), (4) Date: Oct. 19, 2001

(87) PCT Pub. No.: WO99/67393

PCT Pub. Date: Dec. 29, 1999

(51) Int. Cl.
*C07K 14/025* (2006.01)
*C07K 14/0005* (2006.01)
*C07K 1/00* (2006.01)
*C12N 15/00* (2006.01)
*C12N 5/06* (2006.01)
*C12N 15/861* (2006.01)
*C12N 15/64* (2006.01)
*C07K 16/00* (2006.01)

(52) U.S. Cl. .................. 530/350; 530/300; 530/388.22; 530/387.9; 435/455; 435/320.1; 435/325; 435/91.4; 424/93.2; 424/93.1

(58) Field of Classification Search .................. 530/350, 530/300, 388.22, 387.8; 435/69.1, 91.4, 435/320.1, 455, 91.41, 91.42; 536/23.1, 536/24.2; 424/93.2, 93.1
See application file for complete search history.

(56) References Cited

U.S. PATENT DOCUMENTS

| 5,276,136 A | 1/1994 | Skubitz et al. |
| 6,491,907 B1 | 12/2002 | Rabinowitz et al. |
| 2001/0031463 A1 | 10/2001 | Kleinschmidt et al. |
| 2002/0192823 A1 | 12/2002 | Bartlett |

FOREIGN PATENT DOCUMENTS

| WO | WO 95/23867 | 9/1995 |
| WO | WO 96/00587 | 1/1996 |
| WO | WO 97/08298 | 3/1997 |
| WO | WO 97/38723 | 10/1997 |
| WO | WO 99/67393 | 12/1999 |

OTHER PUBLICATIONS

Kmiec, E. B. Gene Therapy. May-Jun. 1999. American Scientist, vol. 87, pp. 240-247.*
Anderson, W.F, Human Gene Therapy. Apr. 1998. Nature, vol. 392, pp. 25-30.*
Verma, I.M. and Somia, N. Gene Therapy- promises, problems and prospect. Sep. 1997. Nature, vol. 389, pp. 239-242.*
Meng R.D. and El-Deiry, W.S. Tumor Suppressor Genes as Targets for Cancer Gene Therapy. 1999. Gene Therapy of Cancer,Chapter 1. pp. 3-18.*
Buning et al, Receptor targeting of adeno-associated virus vectors, Gene Therapy (2003), vol. 10, pp. 1142-1151.*
Smith and Zhang, The challenges of genome sequence annotation or "The devil is in the details", Nature Biotechnology, (1997) vol. 15, pp. 1222-1223.*
Tseng and Liang, Evolutionary model for predicting protein function by matching local surfaces: a Bayesian Monte Carlo approach, poster abstract downloaded Jun. 9, 2005.*
Reid et al, Adeno-Associated Virus Capsids Displaying Immunoglobin-Binding Domains Permit Antibody-Mediated Vector Retargeting to Specific Cell Surface Receptors, JVI, 2002, vol. 76, pp. 4559-4566.*
Russell, S.J. Replicating Vectors for Gene Therapy of Cancer: Risks, Limitations and Prospects. 1994. European J. of Cancer vol. 30(A). pp. 1165-1171.*
Bartlett et al., (1999), "Targeted Adeno-associated Virus Vector Transduction of Nonpermissive Cells Mediated By A Bispecific F (ab'γ)$_2$ Antibody," *Nat. Biotechnol.*, 17:181-186.
Cosset et al., (1996), "Targeting Retrovirus Entry," *Gene Ther.*, 3:946-956.
Douglas et al., (1996), "Targeted Gene Delivery By Tropism-modified Adenoviral Vectors," *Nat. Biotechnol.*, 14:1574-1578.
Girod et al., (1999), "Genetic Capsid Modifications Allow Efficient Re-targeting of Adeno-associated Virus Type 2," *Nature Medicine*, 5:1052-1056.
Krasnykh et al., (1996), "Generation of recombinant Adenovirus Vectors with Modified Fibers for Altering Viral Tropism," *J. Virol.*, 70:6839-6846.
Ohno et al., (1997), "Cell-specific Targeting of Sindbis Virus Vectors Displaying IgG-binding Domains of Protein A," *Nat. Biotechnol.*, 15:763-767.
Ruffing et al., (1994), "Mutations in the Carboxy Terminus of Adeno-associated Virus 2 Capsid Proteins Affect Viral Infectivity: Lack of an RGD Integrin-binding Motif," *J. Gen. Virol.*, 75:3385-3392.
Steinbach et al., (1997), "Assembly of Adeno-associated Virus Type 2 Capsids In Vitro," *Biol. Abstr.*, 104, Ref. 46570.
Stevenson et al., (1997), "Selective Targeting of Human Cells by a Chimeric Adenovirus Vector Containing a Modified Fiber Protein," *J. Virol.*, 71:4782-4790.
Yang et al., (1998), "Development of Novel Cell Surface CD34-targeted Recombinant Adenoassociated Virus Vectors for Gene Therapy," *Hum. Gene Ther.*, 9:1929-1937.
Wickham et al., (1996), "Adenovirus Targeted to Heparan-containing Receptors Increases its Gene Delivery Efficiency to Multiple Cell Types," *Nat. Biotechnol.*, 14:1570-1573.

(Continued)

*Primary Examiner*—Joseph Woitach
*Assistant Examiner*—Maria Marvich
(74) *Attorney, Agent, or Firm*—Clark & Elbing LLP

(57) ABSTRACT

The invention relates to a structural protein of adeno-associated virus (AAV) which comprises at least one mutation which brings about an increase in the infectivity of the virus.

15 Claims, 4 Drawing Sheets

OTHER PUBLICATIONS

Figure 1:
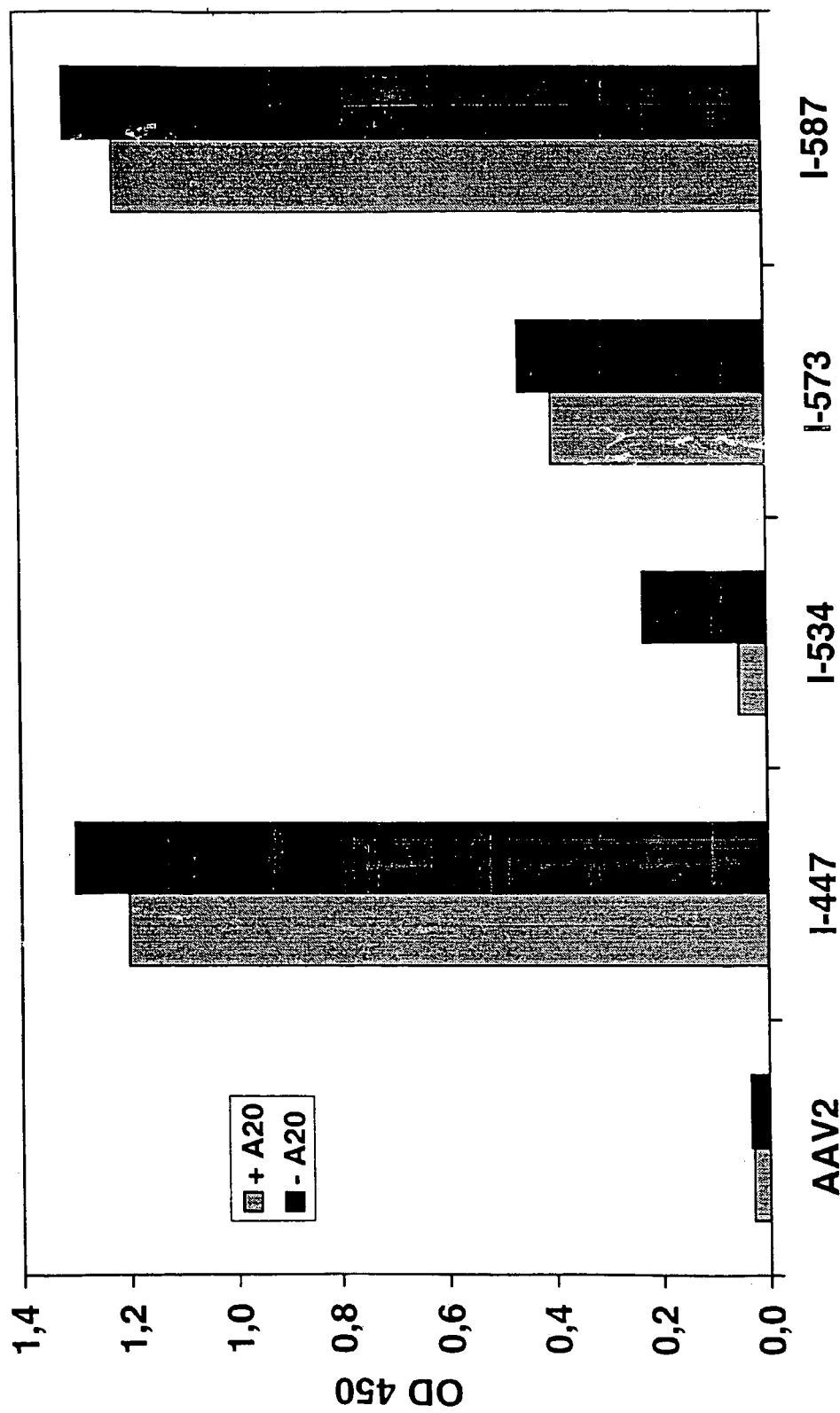

Aumailley et al., "Identification of the Arg-Gly-Asp Sequence in Laminin A Chain as a Latent Cell-Binding Site Being Exposed in Fragment P1," *FEBS* 262:82-86 (1990).

Chapman et al., "Structure, Sequence, and Function Correlations Among Parvoviruses," *Virology* 194:491-508 (1993).

Chiorini et al., "High-Efficiency Transfer of the T Cell Co-Stimulatory Molecular B7-2 to Lymphoid Cells Using High-Titer Recombinant Adeno-Associated Virus Vectors," *Human Gene Therapy* 6:1531-1541 (1995).

Hermonat et al., "Genetics of Adeno-Associated Virus: Isolation and Preliminary Characterization of Adeno-Associated Virus Type 2 Mutants," *Journal of Virology* 51:329-339 (1984).

Luo et al., "Preliminary X-Ray Crystallographic Analysis of Canine Parvovirus Crystals," *J. Mol. Biol.* 200:209-211 (1988).

Kotin, "Prospects for the Use of Adeno-Associated Virus as a Vector For Human Gene Therapy," *Human Gene Therapy* 5:793-801 (1994).

Muzyczka, "Use of Adeno-Associated Virus as a General Transduction Vector for Mammalian Cells," *Current Topics in Microbiology and Immunology* 158:97-129 (1992).

Nimako et al., "Human Papillomavirus-Specific Cytotoxic T Lymphocytes in Patients with Cervical Intraepithelial Neoplasia Grade III," *Cancer Research* 57:4855-4861 (1997).

Ruffing et al., "Assembly of Viruslike Particles by Recombinant Structural Proteins of Adeno-Associated Virus Type 2 in Insect Cells," *Journal of Virology* 66:6922-6930 (1992).

Rutledge et al., "Infections Clones and Vectors Derived from Adeno-Associated Virus (AAV) Serotypes Other Than AAV Type 2," *Journal of Virology* 72:309-319 (1998).

Srivastava et al., "Nucleotide Sequence and Organization of the Adeno-Associated Virus 2 Genome," *Journal of Virology* 45:555-564 (1983).

Tarpey et al., "Human Cytotoxic T Lymphocytes Stimulated by Endogenously Processed Human Papillomavirus Type 11 E7 Recognize a Peptide Containing a HLA-A2 (A*0201) Motif," *Immunology* 81:222-227 (1994).

Tsao et al., "The Three-Dimensional Structure of Canine Parvovirus and Its Functional Implications," *Science* 251:1456-1464 (1991).

Valsesia-Wittmann et al., Modifications in the Binding Domain of Avian Retrovirus Envelope Protein to Redirect the Host Range of Retroviral Vectors, *Journal of Virology* 68:4609-4619 (1994).

Wickham et al., "Increased In Vitro and In Vivo Gene Transfer by Adenovirus Vectors Containing Chimeric Fiber Proteins," *Journal of Virology* 71:8221-8229 (1997).

Wistuba et al., "Subcellular Compartmentalization of Adeno-Associated Virus Type 2 Assembly," *Journal of Virology* 71:1341-1352 (1997).

Wistuba et al., "Intermediates of Adeno-Associated Virus Type 2 Assembly: Identification of Soluble Complexes Containing Rep and Cap Proteins," *Journal of Virology* 69:5311-5319 (1995).

Wu et al., "The Canine Parvovirus Empty Capsid Structure," *J. Mol. Biol.* 233:231-244 (1993).

Shi et al., "Insertional Mutagenesis of the Adeno-Associated Virus Type 2 (AAV2) Capsid Gene and Generation of AAV2 Vectors Targeted to Alternative Cell-Surface Receptors," *Human Gene Therapy* 12:1697-1711 (2001).

"Designer Gene Therapy May Target Specific Body Area," *Gene Therapy, Business News*, Jan. 20, 2003. vol. 2, p. 1-8.

Marshall, "Second Child In French Trial is Found to Have Leukemia," *Science* 299:320 (2003).

Shi et al., "RGD Inclusion of VP3 Provides Adeno-Associated Virus Type 2 (AAV2)-Based Vectors with a Heparan Sulfate-Independent Cell Entry Mechanism," *Molecular Therapy* 7:515-525 (2003).

Steinbach et al., "Assembly of Adeno-Associated Virus Type 2 Capsids in vitro," *Journal of General Virology* 78:1453-1462 (1997).

White et al., Targeted Gene Delivery to Vascular Tissue In Vivo by Tropism-Modified Adeno-Associated Virus Vectors, *Circulation* 109:513-519 (2004).

Anderson, "Human Gene Therapy," *Nature* 392:25-30 (1998).

Asokan et al., "AAV Does the Shuffle," *Nature Biotechnology* 24:158-160 (2006).

Buning et al., "Receptor Targeting of Adeno-Associated Virus Vectors," *Gene Therapy* 10:1142-1151 (2003).

Grifman et al., "Incorporation fo Tumor-Targeting Peptides into Recombinant Adeno-Associated Virus Capsids," *Molecular Therapy* 3:964-975 (2001).

Hoque et al., "Nuclear Transport of the Major Capsid Protein is Essential for Adeno-Associated Virus Capsid Formation," *Journal of Virology* 73:7912-7915 (1999).

Huttner et al., "Genetic Modifications of the Adeno-Associated Virus Type 2 Capsid Reduce the Affinity and the Neutralizing Effects of Human Serum Antibodies," *Gene Therapy* 10:2139-2147 (2003).

Kmiec, "Gene Therapy," *American Scientist* 87:240-247 (1999).

Maass et al., "Recombinant Adeno-Associated Virus for the Generation of Autologous, Gene-Modified Tumor Vaccines: Evidence for a High Transduction Efficiency into Primary Epithelial Cancer Cells," *Human Gene Therapy* 9:1049-1059 (1998).

Maheshri et al., "Directed Evolution of Adeno-Associated Virus Yields Enhanced Gene Delivery Vectors," *Nature Biotechnology* 24:198-204 (2006).

Meng et al., "Tumor Suppressor Genes as Targets for Cancer Gene Therapy," *Gene Therapy of Cancer* Chapter 1, pp. 3-18 (1999).

Mizukami et al., "Adeno-Associated Virus Type 2 Binds to a 150-Kilodalton Cell Membrane Glycoprotein," *Virology* 217:124-130 (1996).

Moskalenko et al., "Epitope Mapping of Human Anti-Adeno-Associated Virus Type 2 Neutralizing Antibodies: Implications for Gene Therapy and Virus Structure," *Journal of Virology* 74:1761-1766 (2000).

Nicklin et al., "Efficient and Selective AAV2-Mediated Gene Transfer Directed to Human Vascular Endothelial Cells," *Molecular Therapy* 4:174-181 (2001).

Perabo et al., "In Vitro Selection of Viral Vectors with Modified Tropism: The Adeno-Associated Virus Display," *Molecular Therapy* 8:151-157 (2003).

Qing et al., "Human Fibroblast Growth Factor Receptor 1 is a Co-Receptor for Infection by Adeno-Associated Virus 2," *Nature Medicine* 5:71-77 (1999).

Ried et al., "Adeno-Associated Virus Capsids Displaying Immunoglobulin-Binding Domains Permit Antibody-Mediated Vectors Retargeting to Specific Cell Surface Receptors," *Journal of Virology* 76:4559-4566 (2002).

Russell,"Replicating Vectors for Gene Therapy of Cancer: Risks, Limitations and Prospects," *European Journal of Cancer* 30A:1165-1171 (1994).

Shi et al., "Insertional Mutagenesis of the Adeno-Associated Virus Type 2 (AAV2) Capsid Gene and Generation of AAV2 Vectors Targeted to Alterntative Cell-Surface Receptors," *Human Gene Therapy* 12:1697-1711 (2001).

Shi et al., "RGD Inclusion of VP3 Provides Adeno-Associated Virus Type 2 (AAV2)-Based Vectors with a Heparan Sulfate-Independent Cell Entry Mechanism," *Molecular Therapy* 7:515-525 (2003).

Smith et al., "The Challenges of genome Sequence Annotation or the Devil is in the Details," *Nature Biotechnology*, 15:1222-1223 (1997).

Spear et al., "Evidence for Two Nucleotide Sequence Orientations Within the Terminal Repetition of Adeno-Associated Virus DNA," *Journal of Virology* 24:627-634 (1977).

Starovasnik et al., "Structural Mimicry of a Native Protein by a Minimized Binding Domain," *Proc. Natl. Acad. Sci. USA* 94:10080-10085 (1997).

Summerford et al., "Membrane Associated Heparan Sulfate Proteoglycan is a Receptor for Adeno-Associated Virus Type 2 Virions," *Journal of Virology* 72:1438-1445 (1998).

Summerford et al., "αVβ5 Integrin: A Co-receptor for Adeno-Associated Virus Type 2 Infection," *Nature Medicine* 5:78-82 (1999).

Tseng et al., "Evolutionary Model for Predicting Protein Function by Matching Local Surfaces: a Bayesian Monte Carlo Approach," The Ninth Annual Conference on Research in Computational Molecular Biology, May 14-18, 2005.

Verma et al., "Gene Therapy-Promises, Problems and Prospects," *Nature* 389:239-242 (1997).

Wendtner et al., "Efficient Gene Transfer of CD40 Ligand into Primary B-CLL cells using recombinant Adeno-Associated Virus (rAAV) Vectors," *Blood* 100:1655-1661 (2002).

White et al., "Designer Gene Therapy May Target Specific Body Area," *Business News* 2:1-2 (2003).

White et al., "Targeted Gene Delivery to Vascular Tissue in Vivo by Tropism-Modified Adeno-Associated Virus Vectors," *Circulation* 109:513-519 (2004).

Wobus et al., "Monoclonal Antibodies Against the Adeno-Associated Virus Type 2 (AAV-2) Capsid: Epitope Mapping and Identification of Capsid Domains Involved in AAV-2-Cell Interaction and Neutralization of AAV-2 Infection," *Journal of Virology* 74:9281-9293 (2000).

Wu et al., "Mutational Analysis of the Adeno-Associated Virus Type 2 (AAV2) Capsid Gene and Construction of AAV2 Vectors with Altered Tropism," *Journal of Virology* 74:8635-8647 (2000).

\* cited by examiner

AAV SCLEROPROTEIN, PRODUCTION AND USE THEREOF

CROSS-REFERENCE TO RELATED APPLICATIONS

This application is the U.S. National Stage of International Application No PCT/EP99/04288, filed Jun. 21, 1999, which claims the benefit of German Application No. DE 198 27 457.2, filed Jun. 19, 1998.

The present invention relates to a structural protein of adeno-associated virus (AAV) which comprises at least one mutation which brings about an increase in the infectivity.

The AAV virus belongs to the family of parvoviruses. These are distinguished by an icosahedral, non-enveloped capsid which has a diameter of 18 to 30 nm and which contains a linear, single-stranded DNA of about 5 kb. Efficient replication of AAV requires coinfection of the host cell with helper viruses, for example with adenoviruses, herpesviruses or vaccinia viruses. In the absence of a helper virus, AAV enters a latent state, the viral genome being capable of stable integration into the host cell genome. The property of AAV integrating into the host genome makes it particularly interesting as a transduction vector for mammalian cells. In general, the two inverted terminal repeats (ITR) which are about 145 bp long are sufficient for the vector functions. They carry the "cis" signals necessary for replication, packaging and integration into the host cell genome. For packaging in recombinant vector particles, a vector plasmid which carries the genes for nonstructural proteins (Rep proteins) and for structural proteins (Cap proteins) is transfected into cells suitable for packaging, for example HeLa or 293 cells, which are then infected, for example, with adenovirus. A lysate containing recombinant AAV particles is obtained after some days.

The AAV capsid consists of three different proteins: VP1, VP2 and VP3, whose relative proportions are 5% VP1, 5% VP2 and 90% VP3. The AAV capsid genes are located at the right-hand end of the AAV genome and are encoded by overlapping sequences of the same open reading frame (ORF) using different start codons. The VP1 gene contains the whole VP2 gene sequence, which in turn contains the whole VP3 gene sequence with a specific N-terminal region. The fact that the overlapping reading frames code for all three AAV capsid proteins is responsible for the obligatory expression of all capsid proteins, although to different extents.

The molecular masses of the capsid proteins are 87 kD for VP1, 73 kD for VP2 and 62 kD for VP3. The sequences of the capsid genes are described, for example, in Srivastava, A. et al. (1983), J. Virol., 45, 555-564; Muzyczka, N. (1992), Curr. Top. Micro. Immunol., 158, 97-129, Ruffing, N. et al. (1992), J. Virol., 66, 6922-6930 or Rutledge, E. A. et al. (1998) J. Virol. 72, 309-319. The physical and genetic map of the AAV genome is described, for example, in Kotin, R. M. (1994), Human Gene Therapy, 5, 793-801.

Also known are various AAV serotypes, of which the human AAV serotype 2 (AAV2) represents a virus vector with advantageous properties for somatic gene therapy. The essential advantages are the lack of pathogenicity for humans, the stable integration of viral DNA into the cellular genome, the ability to infect non-dividing cells, the stability of the virion, which makes purification to high titres ($10^{11}$ particles per ml) possible, the low immunogenicity, and the substantial absence of viral genes and gene products in the recombinant AAV vector, which is advantageous from the viewpoint of safety for use in gene therapy. The cloning of genes into the AAV vector now takes place by methods generally known to the skilled person, as described, for example, in WO 95/23 867, in Chiorini J. A. et al. (1995), Human Gene Therapy, 6, 1531-1541 or in Kotin, R. M. (1994), supra.

AAV2 for example has in general a broad active spectrum. Epithelial tissues, such as human epithelial tumour cell lines, but also primary tumour material such as cervical or ovarian carcinoma or melanoma, and human keratinocytes are infected very efficiently (70-80%), whereas haematopoietic cells such as lymphohaemopoietic cells are infected with 10- to 100-fold lower efficiency (0.5-5%) (Mass et al. (1998) Human Gene Therapy, 9, 1049-1059). One reason for this might be that an interaction between AAV and an AAV receptor on the surface of the cell is necessary for uptake of AAV into the cell. Thus, for example, the putative primary AAV2 receptor is a cell membrane glycoprotein of 150 kD (Mizukami, H. et al. (1996), Virology, 217, 124-130) or heparan sulphate proteoglycan (Summerford, C. & Samulski, R. J. (1998), J. Virol., 72, 1438-1445). Possible secondary receptors which have been determined are: are: $_\alpha V_\beta 5$ integrin (Summerford et al., (1999) Nature Medicine 5, 78-82) and human fibroblast growth factor receptor 1 (Qing et al., (1999) Nature Medicine 5, 71-77). Binding studies have now shown that the surface density of this receptor is reduced on cells which are inefficiently infected by AAV2.

It is now known that it is possible to by genetic modification of capsid proteins of retroviruses and adenoviruses to introduce binding sites for receptors which are expressed only on particular cells into a capsid, and thus a receptor-mediated targeting of vectors has been made possible (see, for example, Cosset, F. L. & Russell, S. J. (1996), Gene Ther., 3, 946-956, Douglas, J. T. et al. (1996), Nat. Biotechnol., 14, 1574-1578, Krasnykh, V. N. et al. (1996), J. Virol., 70, 6839-6846, Stevenson, S. C. et al. (1997), J. Virol., 71, 4782-4790 or Wickman, T. J. et al. (1996), Nat. Biotechnol., 14, 1570-1573). WO 96/00587 also refers to AVV capsid fusion proteins which are said to contain heterologous epitopes of clinically relevant antigens, which is said to induce an immune response, and which are said not to interfere with capsid formation. However, the publication contains only a general reference without detailed information on the implementability, in particular on suitable insertion sites. Steinbach et al. (1997) (Biol. Abstr. 104, Ref. 46570) were concerned with the in vitro assembly of AAV particles which had previously been expressed in the baculo system. Mutations are also made on the cap gene, but these are intended not to lead to a change in the tropism but to a plasmid construct in which only one VP protein is expressed in each case. There is no mention of a change in the infectivity. Ruffing et al. (1994) (J. Gen. Virol. 75, 3385-3392) intended to investigate the natural tropism of AAV2. For this purpose, mutations were introduced at the C terminus of the AAV2 VP protein, the basic assumption (erroneous due to incorrect initial data) being to change an RGD motif in this way. The mutation merely brought about reduced infectivity.

Indirect targeting is disclosed in Bartlett et al. (1999; Nat. Biotechnol. 17, 181-186). In this case, there was use of a bispecific antibody which was directed both against the AAV2 capsid and against a target cell. The viral capsid was, however, neither covalently linked nor modified or a capsid protein mutated. The only attempt to date at direct targeting in the case of AAV2 was undertaken by Yang et al. (1998; Hum. Gene Ther. 1, 1929-1937). In this case, single-chain antibody fragments against the CD34 molecule was fused to the N terminus of VP2, inserted directly at the N terminus of VP1. This method has, however, 2 distinct disadvantages. On the one hand, the infection titre was very low and, on the other hand, for successful packaging it was necessary to coexpress the fusion protein with unmutated capsid proteins VP1, VP2 and VP3. However, this resulted in a mixture of chimeric and wild-type capsid proteins, whose composition and thus activity was unpredictable. Moreover, the packaging efficiency and the infectivity via the wild-type receptor of HeLa cells was also considerably reduced compared with the wild type.

One object of the present invention was therefore to modify AAV in such a way that a more specific and more efficient gene transfer is possible than with known AAV vectors.

It has now been found, surprisingly, that structural or capsid proteins of AAV can be modified so that this brings about an increase in infectivity.

One aspect of the present invention is therefore an AAV structural protein which comprises at least one mutation which brings about an increase in the infectivity. It is possible through the increase in infectivity for example to achieve a specific and efficient gene transfer of slightly infected tissue such as, for example, haematopoietic tissue. Changing and, in particular, increasing mean for the purpose of this invention not a general but a cell-specific change or increase, that is to say in relation to a particular cell type. Hence, cases in which the infectivity is reduced for particular cells and is increased only for another cell type or several other cell types are also included under an increase in the infectivity.

The mutation(s) is/are preferably located on the virus surface. For determining the surface-located regions of the structural proteins, it was surprisingly found according to the present invention that CPV and AAV2 sequences and structures are comparable. It is therefore possible to have recourse preferably to known crystal structures of parvoviruses such as of parvovirus B19 or of CPV (canine parvovirus) and to identify, with the aid of homology comparisons, protein domains which are important for the AAV/AAV receptor interaction and which can be modified. According to the present invention, therefore, for example a computer-assisted comparison between CPV and AAV2, and parvovirus B19 and AAV2, have surprisingly led reproducibly to the identification of loops in VP3, whose sequence varies, i.e. which have a low homology and which may be responsible for the tropism and the differences in infectivity of the virus. Thus, the known crystal structure of the CPV VP2 capsid protein (for example Luo M. (1988), J. Mol. Biol., 200, 209-211; Wu and Rossmann (1993), J. Mol. Biol., 233, 231-244) was taken as pattern, because of the great similarity to AAV2 VP3 in the secondary structure of the protein, in order to find the regions which are exposed on the viral capsid surface and, because of the local amino acid sequence, are sufficiently flexible to withstand insertion of a peptide sequence. In this case, care was taken that no secondary structural elements of the AAV2 capsid protein which would destabilize the capsid were selected.

Another possibility for determining the surface-located regions of the structural proteins is to compare the nucleic acid sequences coding for the capsids from different AAV serotypes. It is possible to use for this purpose, for example, known DNA sequences from different AAV serotypes, such as AAV2, AAV3, AAV4 or AAV6, for structural analyses of possible capsid morphologies of, for example, AAV2, it being possible ab initio to calculate possible tertiary structures and assign sequence regions on the basis of generally known amino acid properties to the inner or outer capsid regions. It was thus possible, for example, according to the present invention to establish seven possible insertion sites in the VP3 region of the AAV2 capsid, and these made it possible to insert, for example, a ligand and express it on the viral surface (see below).

In another preferred embodiment, the mutation(s) are located at the N terminus of the structural protein, because it has been found that, for example, in the case of the parvoviruses CPV and B19 the N terminus is located on the cell surface. In this case, the mutation is preferably not carried out directly at the N terminus of VP1 but is carried out a few amino acids downstream from the N terminus.

In another preferred embodiment, the mutation causes a change in the protein-cell membrane receptor interaction, the cell membrane receptor preferably being a glycoprotein of about 150 kD and/or a heparan sulphate proteoglycan, as described above in detail. These two receptors are presumably primary receptors which are supplemented by at least one secondary receptor (see above).

In general, the mutation may be present in the VP1, VP2 and/or VP3 structural protein, with the VP1 structural protein and/or the VP3 structural protein being preferred. The mutated structural protein is furthermore preferably still capable of particle formation, i.e. formation of an icosahedral capsid. The structural protein may furthermore be derived from all AAV serotypes, in particular from human serotypes, preferably from AAV1, AAV2, AAV3, AAV4, AAV5 and/or AAV6, especially from AAV2, AAV3 and/or AAV6. These also include serotypes derived from said serotypes, in particular AAV2.

In another preferred embodiment, the mutation(s) is/are point mutation(s), mutation(s) of several amino acids, one or more deletions and/or one or more insertions, and combinations of these mutations in the structural protein, the insertion preferably being the insertion of a cell membrane receptor ligand, a Rep protein or Rep peptide, for example in the form of a Rep domain, an immunosuppressive protein or peptide and/or a protein or peptide having a signal for double-strand synthesis of the transgene or foreign gene.

Examples of insertions are, inter alia, integrins, cytokines or receptor-binding domains of cytokines or growth factors such as, for example, GM-CSF, IL-2, IL-12, CD40L, TNF, NGF, PDGF or EGF, single-chain antibodies (scFv) binding to cell surface receptors, for example to single-chain antibodies binding to the surface receptors CD40, CD40L, B7, CD28 or CD34, or epitopes or receptor binding sites which are, for example, in turn recognized by particular antibodies, for example anti-CD40L monoclonal antibodies, or by chemical substances or hormones, for example catecholamines. Further examples are also antibodies against particular epitopes such as, for example, cell recognition particles or parts of xenobiotics such as drugs, which are partly presented on the cell surface of particular cells.

In a preferred embodiment, antibody-binding structures such as, for example, protein A, protein G or anti-Fc antibody, or parts thereof, are inserted. To these are coupled in turn specific antibodies against particular cell surface structures (for example against CD40 in the case of lymphatic cells or against CD34 in the case of haematopoietic cells). This makes almost universal use of substances containing the structural protein according to the invention possible, because virtually any antibody could be coupled on, and use can then be very specific too.

With this indirect targeting it is possible to prepare a universal AAV targeting vector which can be loaded individually and, depending on the use, with different antibodies, each of which are directed against different specific surface receptors or surface molecules on the target cell, and via which the virus binds to the target cell and is intended to infect the latter. This makes the individual cloning of different AAV mutants for specific targeting problems unnecessary. It is moreover possible for appropriate vectors or capsid mutants according to the invention also to be used, by employing a wide variety of antibodies, for determining suitable surface receptors on the target cells which are suitable for virus binding or for uptake thereof into the cells, so that it is possible quickly and efficiently to screen targeting receptors on the target cells.

It is particularly preferred to insert one or more times—preferably once—the Z domain of protein A, in particular in truncated, deleted form, for example as Z34C protein (Starovasnik et al. (1997), Proc. Natl. Acad. Sci. USA 16:94, 10080-10085), and, in this case, in some circumstances previously to delete some amino acids at the deletion site in the capsid protein. The Z domain of protein A and successive insertion twice thereof into the capsid of Sindbis viruses as described by Ohno et al. (1997) Nat. Biotech. 15, 763-767. Protein A binds via five independent domains to the FC part of antibodies. The strongest binding domain is the B or Z domain, of which 33 amino acids are essential for the binding. This binding structure can be stabilized by two cysteine bridges (Starovasnik et al. supra).

An example of a particularly preferred ligand is the P1 peptide (QAGTFALRGDNPQG) (SEQ ID NO: 1) which is a peptide 14 amino acids long from the core sequence of an alpha chain of the laminin family. This sequence is sufficient, for example, to recognize an integrin receptor which mediates, inter alia, the endocytosis of viral particles, for example of adenovirus. The P1 peptide binds irrespective of its conformation (linear or circular) to the integrin receptor. According to the present invention, the coding DNA sequence of the P1 peptide is inserted into the gene coding for an AAV Further possible ligands to be inserted at the insertion sites are those which bind merely by their charge, the nature of the characteristic amino acid composition, and/or via their specific glycosylation and/or phosphorylation to cell surface molecules. In this connection, the nature of the characteristic amino acid composition means that these have, for example, predominantly hydrophobic, hydrophilic, sterically bulky, charged amino acid residues or those containing amino, carboxylic acid, SH or OH groups. It is thus possible to make cells susceptible to AAV transfection by a nonspecific mechanism. In this connection, for example, many cell surface molecules are specifically glycosylated and phosphorylated or negatively charged and may thus, for example, represent a target for an AAV mutant with an amino acid ligand with multiple positive charges.

In a further preferred embodiment, the mutation(s) is(are) brought about by insertions at the XhoI cleavage site of the VP1-encoding nucleic acid and in another preferred embodiment at the BsrBI cleavage site of the VP1-encoding nucleic acid. A further preferred embodiment of the structural protein according to the invention is brought about by a deletion between the BsrBI/HindIII cleavage sites of the VP1-encoding nucleic acid and one or more insertions, preferably at the deletion site.

In a further preferred embodiment of the present invention, the mutation(s) is(are) brought about by one or more deletions between the XhoI/XhoI cleavage sites of the VP1-encoding nucleic acid, which comprises 62 amino acids (Hermonat, P. L. et al. (1984), J. Virol., 51, 329-339). In a further preferred and corresponding embodiment, the deletion(s) is/are located between the BsrBI/HindIII cleavage sites of the VP1-encoding nucleic acid, which is located within the deletion described above and comprises 29 amino acids. This deletion has the advantage that it has no overlap with the rep gene and therefore has essentially no effect on the packaging mechanism.

In a further preferred embodiment, one or more insertions are present in the VP3 structural protein (Rutledge, E. A. et al. (1998) supra) before and/or after at least one amino acid in the sequence selected from, YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT EQYGS (SEQ ID NO: 6), LQRGN RQAAT (SEQ ID NO: 7), NVDFT VDTNG (SEQ ID NO: 8), because these sites are located on the exposed sites of a loop, in which case the risk of changing the VP3 structure is low.

The point mutation(s), the mutation(s) of several amino acids, the deletion(s) or insertion(s) is/are carried out by generally known methods by deletion and insertion in the gene coding for the structural protein. The deletions can be introduced into the individual structural protein genes for example by PCR-assisted mutagenesis. The insertions can be introduced by generally known methods, for example by hydrolysis by restriction endonucleases of the appropriate structural protein genes and subsequent ligase reaction.

It is possible relatively easily in an adhesion test (Valsesia-Wittmann, S. et al. (1994) J. Virol. 68, 4609-4619) using suitable cells which express a selected receptor, for example the laminin alpha receptor, but are difficult to infect with wild-type AAV, for example with wild-type AAV2, to detect the change in the infectivity of the mutated structural proteins according to the invention, for example the functional expression of the P1 peptide on the surface of AAV. The advantage of this test system is that it is possible to determine quickly by means of inspection and quantitatively by means of measurement of the optical density, for example, expression of the P1 peptide on the viral surface.

For rapid screening of the expression of inserted ligands on the viral surface and of modifications of the tropism, therefore, a suitable targeting model has been developed on the basis of the laminin/integrin ligand/receptor system. For this purpose, the nucleic acid coding for the P1 peptide, which has already been described in detail above and which binds, irrespective of its conformation (linear or circular), to the integrin receptor has been incorporated into the cap gene so that rAAV with P1 ligands in the capsid (rAAV-P1) is obtained after virus packaging with mutated AAV2 genome. The test system is carried out by using two different cell lines which, on the one hand, can be infected by wild-type AAV2 and express the AAV2 receptor (heparan sulphate proteoglycan receptor, HPR, possibly also secondary receptors (see above)), but not the integrin receptor for laminin P1 (LP1-R), and, on the other hand, which express LP1-R on their surface but not HPR. Suitable cell lines can be identified in flow cytometry investigations using anti-HPR antibodies and adhesion assays on laminin P1.

These tests showed that, for example, the mutants described above infect laminin alpha receptor-positive indicator cells, for example the cell line M07-LP1-R, with an efficiency which is at least 10 times higher than wild-type AAV. It was also shown, for example, in competition assays with soluble P1 peptide that infection with rAAV-P1 was in fact mediated by the inserted ligands. Likewise, in another test with a rAAV-P1 mutant, the transfection of B16F10 cells, a cell line which is normally not infected by wild-type AAV, was more than four orders of magnitude greater than was possible with wild-type AAV.

Another aspect of the present invention is also a structural protein according to the invention in the form of an AAV particle, in particular in the form of an AAV capsid, because particles and capsids are particularly suitable as carriers of selected compounds, for example rAAV transduction vectors.

Further aspects of the present invention are a nucleic acid, preferably an RNA or DNA, in particular a double-stranded DNA, coding for a structural protein according to the invention.

The present invention also relates to a cell, preferably a mammalian cell, for example a COS cell, Hela cell or 293 cell, comprising a nucleic acid according to the invention. Cells of this type are suitable, for example, for preparing the recombinant AAV particles.

A further aspect of the present invention is therefore also a process for preparing a structural protein according to the invention, in particular for preparing a structural protein according to the invention in the form of an AAV particle, where a suitable cell comprising a nucleic acid coding for the structural protein according to the invention is cultivated and, where appropriate, the expressed structural protein is isolated. For example, the structural protein according to the invention can be isolated on a caesium chloride gradient as described, for example, in Chiorini, J. A. et al. (1995), supra.

A further aspect of the present invention relates to the use of the fusion protein according to the invention for altering the tropism of AAV, for transforming a cell, in particular a cell whose susceptibility to AAV infection was previously low, such as, for example, a haematopoietic cell, for gene therapy in the form of suitable rAAV vectors as already described above in detail, or for genomic targeting.

Also included is the use of a fusion protein according to the invention in which the mutation has brought about an increased infectivity for particular cells, for example B16F10 having an integrin receptor, for activity instigations using these cells. Examples are tumour models and tumour cell lines, preferably of murine origin. In this use it is possible to employ for the investigation models which are realistic and comparable for humans and which were not previously accessible in this way, such as certain mouse cell lines. It must be stated in this connection that the susceptibility of mouse cells to infection is generally much worse than that of human cells. Thus, tumours induced in the mouse with B16F10 melanoma cells are not susceptible to AAV2 with unmutated capsid. However, precisely in this case the proteins according to the invention make AAV2 activity studies possible in this and correspondingly other tumour models in mice. An additional facilitating factor is that mouse cells in many tissues and cell types have the specific integrin receptor for the P1 peptide, which is a preferred ligand for the structural proteins mutated according to the invention. It is thus possible with the mutants according to the invention to construct, via the increased infectivity for, for example, B16F10 and other murine tumour cells lines which have, for example, this specific integrin receptor, a test model which is more realistic and more comparable for humans than previously disclosed, because the induced tumours can thus be transduced considerably more efficiently.

Another use of the fusion protein according to the invention is in diagnosis. Thus, it is possible according to the invention for example to employ antibodies or antibody-binding substances with antibodies as ligands, which recognise and bind particular presented epitopes on cells, for example in a blood sample, so that a signal is initiated. Application examples would be presented parts of xenobiotics such as drugs or cell recognition particles, with which it is possible to determine the origin of tissue cells, for example in tumour diagnosis.

Other aspects of the present invention also relate to a medicinal product or a diagnostic aid comprising a fusion protein according to the invention, a nucleic acid according to the invention or a cell according to the invention and, where appropriate, suitable excipients and additives, such as, for example, a physiological saline solution, stabilizers, proteinase inhibitors etc.

A considerable advantage of the present invention is that through the mutagenesis according to the invention of AAV structural proteins the infectivity can be altered essentially without loss of the packaging efficiency of recombinant AAV vectors into the capsid of the virus, in particular the infectivity for cells of low susceptibility, such as, for example, haematopoietic cells, can be increased several times. The present invention is therefore particularly suitable for an improved in vitro and in vivo transformation of particular cells, for example for somatic gene therapy.

It will be apparent to those skilled in the art that various modifications and variations can be made to the compositions and processes of this invention. Thus, it is intended that the present invention cover such modifications and variations, provided they come within the scope of the appended claims and their equivalents.

Priority application DE 198 27 457.2, filed Jun. 19, 1998, including the specification, drawings, claims and abstract, is hereby incorporated by reference. All publications cited herein are incorporated in their entireties by reference.

The following examples and figures are intended to explain the invention in detail without restricting it.

FIG. 1) shows the detection of P1 on the surface of capsid mutants and the wild type either in a direct ELISA (black bars) or in an indirect ELISA (grey bars).

Figure 2:
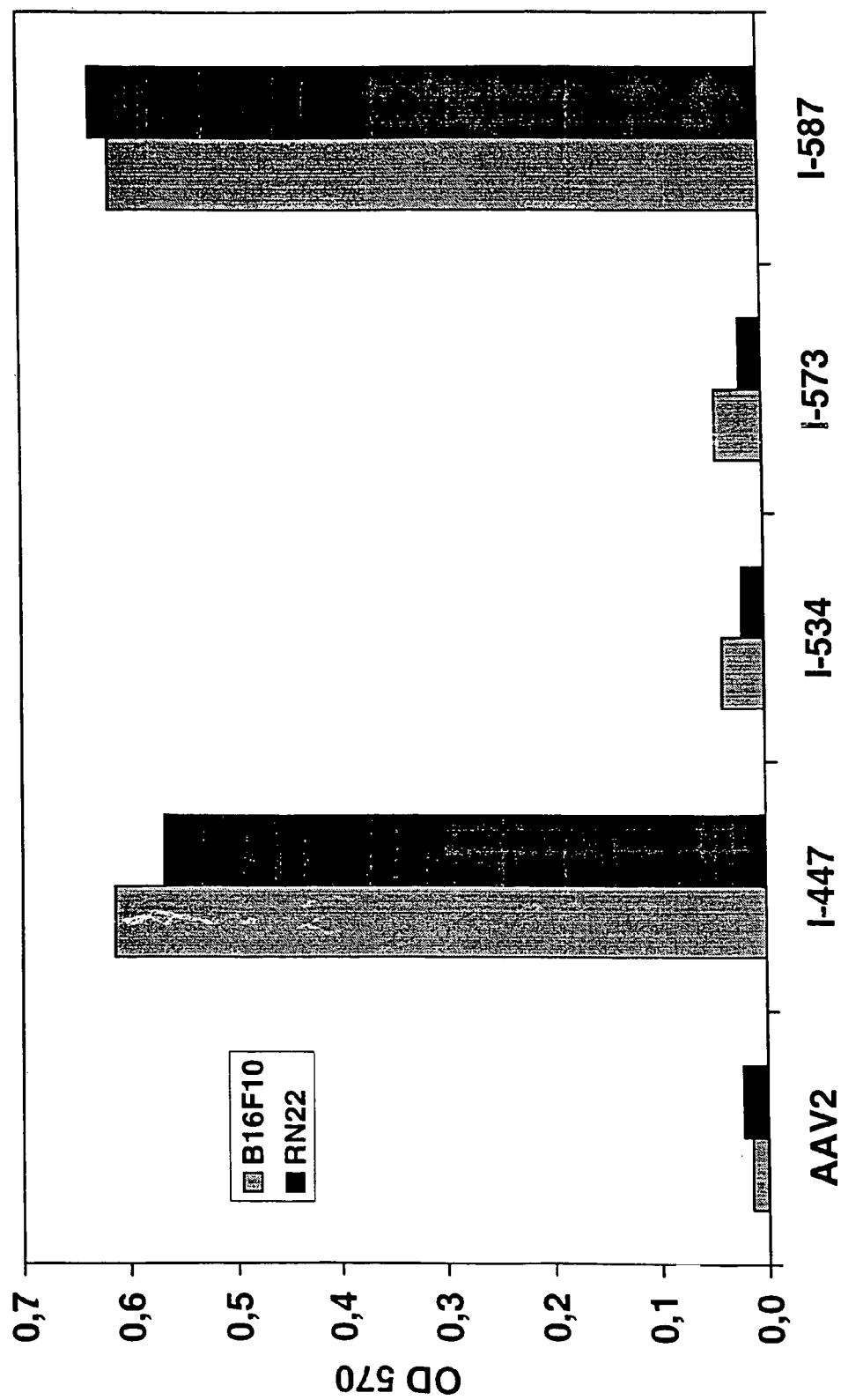

FIG. 2) shows the binding of the capsid mutants or the wild type to various cell types.

Figure 3:
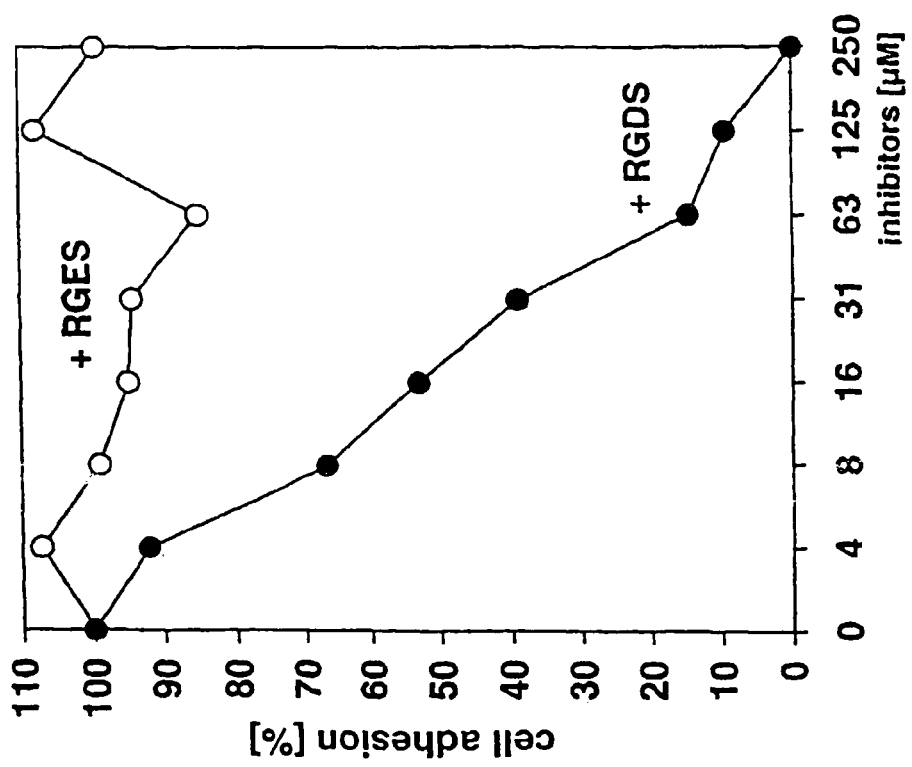

FIG. 3) shows the inhibition of the binding of the capsid mutant I-447 to B16F10 cells.

Figure 4:
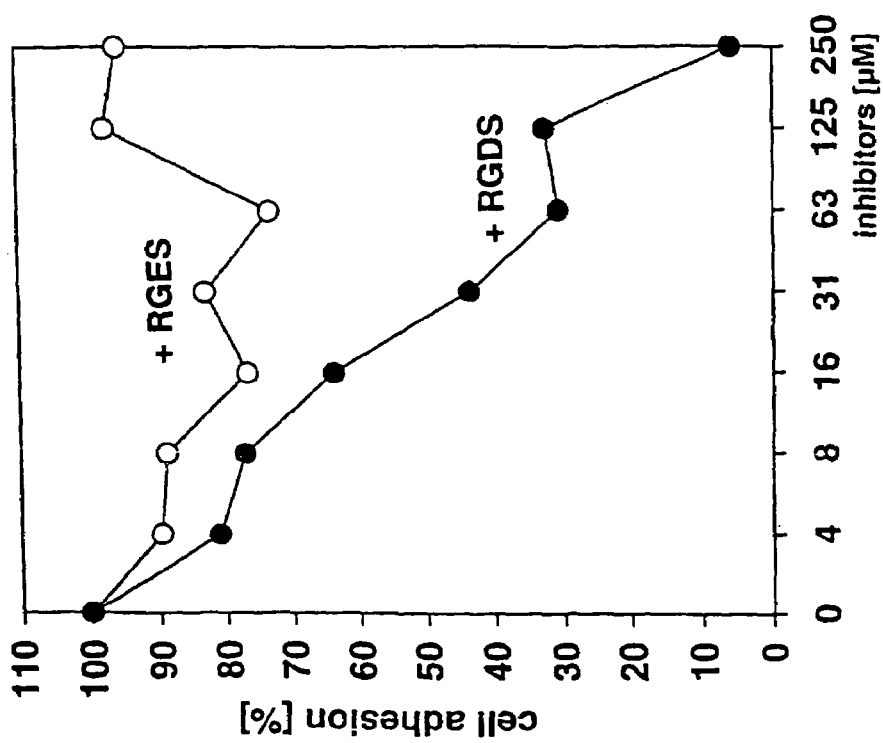

FIG. 4) shows the inhibition of the binding of the capsid mutant I-587 to B16F10 cells.

EXAMPLES

The following mutations were produced by means of PCR-assisted mutagenesis and cutting with the restriction enzymes XhoI, BsrBI and HindIII:

1. Mutations in VP1
   a) deletion between the XhoI/XhoI cleavage sites of VP-1 (ΔXho; 62 amino acids, AA) (Hermonat et al. (1984) Journal of Virology 51, 329-339),
   b) deletion between BsrBI and HindIII cleavage sites of VP-1, which is located within the above deletion a) and comprises 29 AAs (ΔBH);
   c) deletion between BsrBI and HindIII, and insertion of a ligand (P1 peptide) (ΔBH+L); and
   d) pure insertion of the ligand (P1 peptide) at the BsrBI cleavage site (B+L).

2. Mutations in VP3
   a) ins447; YYLSR TNTPS(CPV: 300) (SEQ ID NO: 4)
   b) INS534; EEKFF PQSGV (CPV: 390) (SEQ ID NO: 5)
   c) ins573; NPVAT EQYGS (CPV: 426) (SEQ ID NO: 6)
   d) ins587; LQRGN RQAAT (CPV: 440) (SEQ ID NO: 7)
   e) ins713; NVDFT VDTNG (CPV: 565) (SEQ ID NO: 8)
   CPV means here the location in the equivalent CPV capsid (Named according to the number of amino acids (AAs) counted after the AA at the start of the N terminus in the VP-1 of AAV2, flanked by in each case 5 amino acids located N-terminally thereof and 5 amino acids located C-terminally thereof; the AA after which the insertion was introduced is shown bold).

It is also possible likewise to introduce an insertion into the five directly adjacent AAs located next to the bold AA, because these are likewise located within a loop in the AAV2 capsid.

3. Characterization of the Capsid Mutants

After carrying out the mutations in the AAV2 genome and packaging the mutated viruses with LacZ reporter gene, the physical vector titres were determined by dot-blot and capsid titres with A20 antibody ELISA, and initial infection tests were carried out on HeLa cells. It was possible thereby to determine whether the mutations disturb the structure of the VP proteins or the interaction between different VP proteins so much that packaging does not occur or infection of the target cell is impaired (Table 1).

TABLE 1

Packaging efficiency of the virus mutants prepared

| Value stock | Physical virus titres | Capsid titres (ELISA with A20 MAb) |
|---|---|---|
| Wild-type capsid | $1 \cdot 10^{12}$ | $1 \cdot 10^{11}$ |
| VP1 mutants | | |
| ΔXho | $6 \cdot 10^{12}$ | $5 \cdot 10^{10}$ |
| ΔBH | $8 \cdot 10^{11}$ | $4 \cdot 10^{9}$ |
| ΔBH + L | $1 \cdot 10^{13}$ | $5 \cdot 10^{10}$ |
| B + L | $3 \cdot 10^{12}$ | $5 \cdot 10^{9}$ |
| VP3 mutants | | |
| 300 (I-447) | $1 \cdot 10^{12}$ | $4 \cdot 10^{10}$ |
| 390 (I-534) | $1 \cdot 10^{10}$ | $1 \cdot 10^{7}$ |
| 426 (I-573) | $3 \cdot 10^{10}$ | $1 \cdot 10^{7}$ |
| 440 (I-587) | $1 \cdot 10^{12}$ | $2 \cdot 10^{10}$ |
| 565 (I-713) | $5 \cdot 10^{10}$ | $1 \cdot 10^{7}$ |

The physical virus titres (dot-blot) and capsid titres (A20 capsid ELISA) are shown. The concentrations are stated in particles/ml.

Result:

It was possible to show for all 4 VP1 mutants, which are recombinant vectors with LacZ transgene, that mutations do not affect the packaging efficiency, and all mutated viruses can be packaged with good titres similar to those of vectors with unmutated capsid (~$10^{12}$ particles/ml). The AAV vectors with mutations in the VP3 region were also able to be packaged successfully with LacZ reporter gene ($10^{10}$-$10^{12}$ physical particles/ml).

4. Binding of rAAV-P1 to Laminin Receptor-Positive Indicator Cells

The adhesion tests described above in detail showed that the above mutants infect, in at least one case, the laminin alpha-receptor-positive indicator cells, for example the M07-LP1-R cell line, with an efficiency which is at least 10 times higher than wild-type AAV. It was additionally found in competition assays with soluble P1 peptide that infection with rAAV-P1 is in fact mediated by the inserted ligand.

5. P1 Mutation in VP3

The initial staring point was a plasmid pUC-AV2 which was prepared by subcoloning of the 4.8 kb BglII fragment of pAV2 (ATCC 37261, ref. 53) into the BamHI cleavage site of pUC19 (New England BioLabs Inc.). Mutations were carried out at defined sites in the plasmid by means of PCR-assisted mutagenesis known to the skilled person. This entailed a sequence coding for P1, a 14 AA peptide with the AA sequence, QAGTFALRGDNPQG (SEQ ID NO: 1), which contains the RGD binding motif of a laminin fragment (Aumailly et al. (1990) FEBS Lett. 262, 82-86), being inserted after nucleotides 3543, 3804, 3921, and 3963. This corresponds to an insertion after amino acids 447, 534, 573, and 587 of the AAV2 capsid protein (named according to the number of amino acids (AA) counted after the AA at the start of the N terminus in VP-1 of AAV2). In the subsequent PCR there is use of in each case 2 mutation-specific primers and, as template, a plasmid, pCap, which contains only the cap gene and is formed by cutting out the 2.2 kb 6. Preparation of AAV2 Particle HeLa cells (a human cervical epithelial cell line) were transfected with the plasmids, then incubated for about 20 h and subsequently infected with adenovirus type 5. 72 h after the infection, the cells were disrupted and AAV2 particles were purified on a CsCl gradient.

7. Characterization of the Capsid Mutants from Example 5

These experiments were intended to find out whether the capsid mutants are able to package the viral genome and form complete capsids. AAV2 particles of the mutants from Example 5 were first checked to find whether and, if yes, how many particles harbour the viral genome and how much DNA was packaged in the capsid mutants. For this purpose, the viruses (mutants and wild type) purified as in Example 6 were treated with DNAse, blotted and hybridized with a Rep probe. The titres shown in Table 2 are titres of AAV2 particles with mutated capsid and wild-type gene, which harbours the corresponding ligand insertion, in contrast to Table 1, which shows the titre of AAV2 mutants with LacZ reporter gene (transgene). The titre resulting from this showed no qualitative difference by comparison with the wild type, although quantitative differences are evident, but they are in turn so small that no domains essential for the packaging can be functionally switched off by the mutations (see Table 2).

It was not possible to read from these results any information about the conformation of the capsid. In a further experiment, A20 monoclonal antibodies (A20MAb) were employed in an ELISA. A20MAb reacts specifically only with completely assembled AAV2 capsid, not with free capsid protein (Wistuba et al., (1997), J. Virol. 71, 1341-1352). The results thereof are also shown in Table 2. Once again, the titre resulting therefrom shows no crucial quantitative or qualitative difference by comparison with the wild type. This shows that the insertions took place on structurally irrelevant loops, and insertion of P1 there had not initiated any change. It was possible to divide the mutations into two groups in relation to their ability of forming DNA-containing particles (Table 2): in one group (mutants I-447 and I-587), the ability to form DNA-containing particles corresponded to the wild-type AVV2. In the second group, this ability was two orders of magnitude less (mutants I-534 and I-573). It was possible to confirm these results by electron microscope analysis.

TABLE 2

Packaging efficiency of the prepared viral mutants from Example 5

| Virus stock | Physical virus titers | Capsid titers ELISA with A20 MAb) |
|---|---|---|
| Wild-type capsid | $8.10^{13}$ | $6.10^{12}$ |
| Mutants | | |
| I-447 | $1.10^{13}$ | $8.10^{11}$ |
| I-534 | $5.10^{11}$ | $3.10^{10}$ |
| I-573 | $1.10^{13}$ | $1.10^{11}$ |
| I-587 | $4.10^{13}$ | $3.10^{12}$ |

The physical virus titres (dot-blot) and capsid titres (A20 capsid ELISA) are shown. The concentrations are stated in particles/ml.

8. Expression of P1 on the Capsid Surface

It was subsequently investigated whether P1 is exposed on the capsid surface. This was done by carrying out two different ELISAs with anti-P1 polyclonal antibodies. In an ELISA which is called "direct", the ELISA plates were coated directly with the virus particle in PBS overnight, blocked and incubated with the anti-P1 polyclonal antibody. Controls were PBS (negative) and a laminin fragment (positive). In the indirect assay, the plates were first coated with A20MAb, and then the virus particles and subsequently the anti-P1 polyclonal antibody were added. In the direct assay, I-447 and I-587 showed a very distinct, whereas I-534 and I-573 showed only a weak, reaction. In the indirect assay, by contrast, I-447, I-587 and I-573 showed a very distinct, whereas I-534 showed absolutely no, reaction (see FIG. 1).

9. Binding of AAV2 Capsid Mutants to Integrin-Expressing Cells

The binding of the mutants to the integrin receptor was determined by a cell adhesion assay which was adapted for viral preparations (Aumailly et al., Supra; Valsesia-Wittmann (1994); J. Virol. 68, 4609-4619). $1\times10^9$ viral particles were coated in 100 µl of PBS directly onto 96-well microtitre plates and blocked with PBS containing 1% BSA. Controls were coated with a laminin fragment with a concentration of 40 µg/ml (positive control) or with BSA (10 mg/ml; negative control). $1\times10^5$ cells per 100 µl were added to the coated wells. They were incubated at 37° in a humidified incubator for 30 minutes for adhesion. At the end of the adhesion time, the wells were washed twice with PBS in order to remove nonadherent cells. Adherent cells were fixed with 100% ethanol for 10 minutes, stained with crystal violet and quantified by an ELISA reader at 570 nm. This time, B16F10 cells and RN22 cell lines were chosen because they expressed P1-specific integrin on their surface and are resistant to AAV2 infections (Maass, G. et al. (1998) Hum. Gen. Ther., 9, 1049-1059; Aumailly et al., supra). Two of the mutations, I-447 and I-587, bound with similarly great efficiency both to B16F10 and RN22 cells. In distinct contrast to this, there was found to be no binding of the wild-type AAV2 and the mutants I-534 and I-573 to these cells (FIG. 2).

In an inhibition assay, cells were mixed with RGDS or RGES, soluble synthetic peptides in varying concentration, (1-250 µmol) before they were loaded onto the plate. This experiment was undertaken in order to test the specificity of the binding of the mutants I-447 and I-587 to B16F10 cells. The cell adhesion test was therefore carried out in the presence of a peptide (RGDS) which competes for the binding site and which corresponds to the active P1 site, and in the presence of an inactive RGES peptide. Both mutations I-447 and I-587 were able to bind with 50% efficiency to B16F10 cells with 30 µmol of the RGDS peptide, whereas the RGES peptide was inactive even at higher concentrations. At a concentration of 250 µmol the RGDS peptide completely suppressed virus binding to B16F10 cells (FIGS. 3 and 4). Similar results were obtained with RN22 cells.

10. Infection Tests with Mutants from Example 5

In order to test the tropism of the capsid mutants I-447 and I-587, cell lines Co-115 and B16F10 were infected with the mutated viruses. Co-115 cells were used to test the wild-type receptor tropism of the virions because these cells can be transduced with wild-type AAV2 and do not bind the P1 peptide. The B16F10 cell line was used for the reasons already mentioned in Example 9. Three days after the infection, the cells were investigated by immuno-fluorescence measurement with the aid of an anti-Rep antibody to find whether the viral Rep protein is expressed (Wistuba et al. (1997) J. Virol. 71, 1341-1352; Wistuba et al. (1995) J. Virol. 69, 5311-5319). Cells were cultured on slides to 70% confluence and incubated with various concentrations of viral preparations according to the invention in serum-free medium together with adenovirus 5. The titres of the viral preparations were determined three days later either by in situ detection of Rep protein synthesis in an immuno-fluorescence assay (Rep titre).

In this case, the immunofluorescence staining with AAV2-infected cells was carried out by a method of Wistuba et al. (Wistuba et al. (1997) J. Virol. 71, 1341-1352; Wistuba et al. (1995) J. Virol. 69, 5311-5319). The slides were washed once with PBS, fixed in methanol (5 min, 4° C.) and then treated with acetone (5 min, 4° C.). The cells were then incubated with the monoclonal antibodies 76-3, which reacts with AAV2 Rep proteins, at room temperature for one hour. This was followed by washing and incubation with a rhodamine-conjugated anti-mouse secondary antibody at a dilution of 1:50 in PBS with 1% BSA for one hour. The titres were calculated from the last limiting dilution of the viral stock solution which had led to fluorescence-positive cells.

Rep-positive CO115 cells were detectable after infection with wild-type AAV2 and with both mutants I-447 and I-587. The infectivitiy of I-587 and I-447 for Co115 cells was two to three orders of magnitude less than that of the wild type (Table 3). Transfection of B16F10 cells was just as inefficient with I-447 as with wild-type virus (Table 3). In clear contrast to this, rep-positive B16F10 cells can be detected after infection with I-587, the titre of the I-587 virus being determined at $1\times10^6$ Rep EFU/ml (Table 3).

In order to investigate whether transfection of B16F10 cells by the mutant I-587 was specifically mediated by the interaction between the P1 sequence on the surface of the mutated capsid and the integrin receptor on the surface of the B16F10 cells, the cells were incubated either with the competing RGDS or with the inactive RGES peptide at concentrations of 200 µmol before infection with the virus. Addition of RGDS peptide neutralized the infectivity of I-587 for B16F10 cells (Table 3), whereas the control peptide RGES had no effect.

TABLE 3

Virus titres on the cell surface

| Virus stock | Titre on CO115 cells | Titre on B16F10 cells – RGDS | Titre on B16F10 cells + RGDS |
|---|---|---|---|
| Wild-type capsid | $2 \cdot 10^9$ | <1 | nd |
| Mutants | | | |
| I-447 | $1 \cdot 10^6$ | <1 | nd |
| I-587 | $1 \cdot 10^7$ | $1 \cdot 10^6$ | <1 |
| rAAV/LacZ | $5 \cdot 10^7$ | <1 | nd |
| rAAV(I-587)/LacZ | $6 \cdot 10^5$ | $5 \cdot 10^4$ | <1 |

The titres on the wild type-susceptible CO115 cells and the wild type-resistant B16F10 cells are shown. The titres are expressed for I-447 and I-587 as for the wild type in Rep EFU/ml and for rAAV/LacZ and rAAV(I-587)/LacZ in LacZ EFU/ml. EFU therein means expression-forming units (Expressing Forming Unit) and nd means "not determined".

In a supplementary experiment, a competition test was carried out with heparin, a receptor analogue, in order to rule out the infection of B16F10 cells by the mutant I-587 being additionally mediated by the primary receptor heparan sulphate proteoglycan. With B16F10 cells no change in the infectious titre, that is to say the infectivity of I-587, was detectable after addition of heparin. In contrast to this it was possible to block completely infection of CO155 cells on addition of 50 µg of heparin and above per ml of infection medium. It follows from this that the infection takes place independently of heparan sulphate proteoglycan via P1 ligands and the integrin receptor.

11. Infection Assay of the Mutants from Example 5 with Galactosidase

In another experiment based on Example 10, rAAV vectors were prepared with a LacZ reporter gene and containing either the wild type (rAAV virion) or I-587 (rAAV(I-587)virion). The viral preparations were called rAAV/LacZ and rAAV(I-587)/LacZ and used to infect B16F10 and CO115 cells (controls).

Infected cells were tested for β-galactosidase expression by X-Gal staining three days after the infection. The X-Gal in situ test for cytochemical staining (LacZ titre) was used in this case. According to this, in order to test the expression of β-galactosidase, the cells were washed once in PBS and fixed with 1.5% glutaraldehyde. The cells were subsequently treated with X-Gal (5-bromo-4-chloro-3-indolyl-p-D-galactopyranoside) as already described by Chiorini et al. (1995) Hum. Gen. Ther. 6, 1531-1541. The titres were calculated from the last limiting dilution of the viral stock solution which led to β-galactosidase-producing cells.

Both virions were infectious in the controls on CO115 cells, although the efficiency of rAAV (I-587)/LacZ was 2 orders of magnitude less. With type B16F10—as expected—no β-galactosidase-positive cells were found after infection with rAAV/LacZ. On the other hand, after infection with rAAV(I-587)/LacZ there were surprisingly found to be a distinctly large number of β-galactosidase-positive cells. The titre of rAAV-(I-587)/LacZ was determined as $5 \times 10^4$ LacZ EFU per ml. The infectivity of rAAV vectors for B16F10 cells was improved by more than four orders of magnitude by the mutation according to the invention (Table 3). In a supplementary experiment, a competition test was carried out with heparin, a receptor analogue, in order to rule out the infection of B16F10 cells by the mutant I-587 being additionally mediated by the primary receptor heparan sulphate proteoglycan. With B16F10 cells no change in the infectious titre, that is to say the infectivity of I-587, was detectable after addition of heparin. In contrast to this it was possible to block completely infection of CO155 cells on addition of 50 µg of heparin and above per ml of infection medium. It follows from this that the infection takes place independently of heparan sulphate proteoglycan via P1 ligands and the integrin receptor.

12. Z34C Protein A Mutation in VP3

Various mutations in VP3 were carried out in analogy to Example 5, at the sites mentioned therein, inserting a sequence coding for the Z34C domain of protein A (Starovasnik 1997 supra) after nucleotides 3543, 3804, 3921 and 3963. At the same time, one or more amino acids located at the insertion site were deleted in each case in order to avoid problems from too long insertions. The mutants are prepared as already detailed in Example 5. Corresponding AAV2 particles were then prepared by the same procedure as in Example 6.

The invention claimed is:

1. An isolated VP1, VP2, VP3 protein of adeno-associated virus 2 (AAV2), which comprises at least one mutation, wherein the mutated structural protein comprises an insertion of amino acids which brings about an increase in the infectivity of an adeno-associated virus (AAV) having the mutated structural protein, wherein the insertion is located directly adjacent to and after the amino acid "N" in LQRGN RQAAT (SEQ ID NO: 7), and wherein said mutated structural protein is capable of particle formation.

2. The VP1, VP2, VP3 protein according to claim 1, wherein the insertions comprises at least one of a cell membrane receptor ligand, a Rep protein or a Rep peptide, or an immunosuppressive protein or an immunosuppressive peptide.

3. The VP1, VP2, VP3 protein according to claim 2, wherein the ligand is selected from an integrin, a cytokine, a receptor-binding domain of a cytokine, a receptor-binding domain of an integrin, a receptor-binding domain of a growth factor, a single-chain antibody that binds to a cell surface receptor, an antibody against cell surface structures, an antibody-binding structure, an antibody-binding epitope, a ligand which binds via its charge, a ligand that binds via the type of amino acids, a ligand that binds via its specific glycosylation, or a ligand that binds via phosphorylation to cell surface molecules.

4. The VP1, VP2, VP3 protein according to claim 1, wherein the structural protein is a component of an AAV particle.

5. The VP1, VP2, VP3 protein of claim 4, wherein the structural protein is a component of an AAV capsid.

6. An isolated nucleic acid VP1, VP2, VP3 protein of adeno-associated virus 2 comprising at least one mutation, wherein the mutated structural protein comprises an insertion of amino acids which brings about an increase in the infectivity of an adeno-associated virus (AAV) having the mutated structural protein, wherein the insertion is located directly adjacent to and after the amino acid "N" in LQRGN RQAAT (SEQ ID NO: 7), and wherein said mutated structural protein is capable of particle formation.

7. An isolated cell comprising the nucleic acid of claim 6.

8. An isolated VP1, VP2, VP3 protein of adeno-associated virus 2, which comprises an insertion of amino acids located directly adjacent to and after the amino acid "N" in LQRGN RQAAT (SEQ ID NO: 7).

9. The VP1, VP2, VP3 protein according to claim 8, wherein the insertion comprises at least one of a cell membrane receptor ligand, a Rep protein or a Rep peptide, or an immunosuppressive protein or an immunosuppressive peptide.

10. The VP1, VP2, VP3 protein according to claim 9, wherein the ligand is selected from an integrin, a cytokine, a receptor-binding domain of a cytokine, a receptor-binding domain of an integrin, a receptor-binding domain of a growth factor, a single-chain antibody that binds to a cell surface receptor, an antibody against cell surface structures, an antibody-binding structure, an antibody-binding epitope, a ligand which binds via its charge, a ligand that binds via the type of amino acids, a ligand that binds via its specific glycosylation, or a ligand that binds via phosphorylation to cell surface molecules.

11. An isolated nucleic acid encoding VP1, VP2, VP3 protein of adeno-associated virus 2 comprising an insertion of amino acids located directly adjacent to and after the amino acid "N" in LQRGN RQAAT (SEQ ID NO: 7).

12. An isolated cell comprising the nucleic acid of claim 11.

13. A process for the preparation of a mutated VP1, VP2, VP3 protein of adeno-associated virus 2 (AAV2), the process comprising of cultivating a cell comprising a nucleic acid coding for a structural protein of adeno-associated virus 2 comprising at least one mutation, wherein the mutated structural protein comprises an insertion of amino acids which brings about an increase in the infectivity of an adeno-associated virus (AAV) having the mutated structural protein, wherein the insertion is located directly adjacent to and after the amino acid "N" in LQRGN RQAAT (SEQ ID NO: 7), and wherein said mutated structural protein is capable of particle formation; and isolating the expressed mutated structural protein.

14. A method for altering the tropism of AAV2, the method comprising cultivating an isolated cell which comprises an AAV2 nucleic acid coding for a mutated VP1, VP2, VP3 protein, wherein the mutated structural protein comprises an insertion of amino acids which brings about an increase in the infectivity of an AAV having the mutated structural protein, wherein the insertion is located directly adjacent to and after the amino acid "N" in LQRGN RQAAT (SEQ ID NO: 7), and wherein said mutated structural protein is capable of particle formation; and isolating the AAV2 particle produced by the cell.

15. A process for the preparation of a mutated VP1, VP2, VP3 protein of adeno-associated virus 2 (AAV2), the process comprising of cultivating a cell comprising a nucleic acid coding for a structural protein of adeno-associated virus 2 comprising an insertion of amino acids located directly adjacent to and after the amino acid "N" in LQRGN RQAAT (SEQ ID NO: 7), and isolating the expressed mutated structural protein.

* * * * *

UNITED STATES PATENT AND TRADEMARK OFFICE
CERTIFICATE OF CORRECTION

PATENT NO. : 7,314,912 B1
APPLICATION NO. : 09/720066
DATED : January 1, 2008
INVENTOR(S) : Hallek et al.

It is certified that error appears in the above-identified patent and that said Letters Patent is hereby corrected as shown below:

On Title Page, under U.S. PATENT DOCUMENTS, replace "2001/0031463" with --2001/031463--.

Column 2, Line 21, replace "determined are: are:" with --determined are:-- ;

Line 37, replace "AVV" capsid" with --AAV capsid--.

Column 5, Line 36, replace "AAV" with --AAV structural protein which is located, for example, on a helper plasmid. Packaging with the mutant helper plasmid results in recombinant AAV with P1 in the capsid (rAAV-P1).--.

Column 8, Line 61, replace "YYLSR" with --YYLSR--;

Line 62, replace "EEKFF" with --EEKFF--;

Line 63, replace "NPVAT" with --NPVAT--;

Line 64, replace "LQRGN" with --LQRGN--;

Line 65, replace "NVDFT" with --NVDFT--.

Column 10, Line 19, replace "2.2 kb" with --2.2 kb EcoRI-BspMI fragment from pUC-Av2 and inserting it into the EcoRI cleavage site of pUC19. The PCR products are then amplified in bacteria and sequenced, and the 1.4 kb EcoNI-XcmI fragment which contains P1 is subcloned in pUC-AV2 in which the corresponding wild-type cap sequence has been cut out. Accordingly, the plasmids (mutants) called after the AA insertion sites pI-447, PI-534, pI-573 and pI-587 contained the complete AAV2 genome.--.

Column 17, Claim 2, Line 23, replace "insertions" with --insertion--.

Signed and Sealed this
Twenty-fifth Day of September, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 14
<212> TYPE: PRT
<213> ORGANISM: Artificial Sequence
<220> FEATURE:
<223> OTHER INFORMATION: Mutated adeno-associated virus VP3 protein

<400> SEQUENCE: 1

Gln Ala Gly Thr Phe Ala Leu Arg Gly Asp Asn Pro Gln Gly
1               5                   10

<210> SEQ ID NO 2
<211> LENGTH: 10

```
<212> TYPE: PRT
<213> ORGANISM: Artificial Sequence
<220> FEATURE:
<223> OTHER INFORMATION: Mutated adeno-associated virus VP3 protein

<400> SEQUENCE: 2

Tyr Lys Gln Ile Ser Ser Gln Ser Gly Ala
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Mutated adeno-associated virus VP3 protein

<400> SEQUENCE: 3

Tyr Leu Thr Leu Asn Asn Gly Ser Gln Ala
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Mutated adeno-associated virus VP3 protein

<400> SEQUENCE: 4

Tyr Tyr Leu Ser Arg Thr Asn Thr Pro Ser
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Mutated adeno-associated virus VP3 protein

<400> SEQUENCE: 5

Glu Glu Lys Phe Phe Pro Gln Ser Gly Val
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Mutated adeno-associated virus VP3 protein

<400> SEQUENCE: 6

Asn Pro Val Ala Thr Glu Gln Tyr Gly Ser
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Mutated adeno-associated virus VP3 protein

<400> SEQUENCE: 7

Leu Gln Arg Gly Asn Arg Gln Ala Ala Thr
 1               5                  10

<210> SEQ ID NO 8
<211> LENGTH: 10
<212> TYPE: PRT
```

-continued

```
<213> ORGANISM: Artificial Sequence
<220> FEATURE:
<223> OTHER INFORMATION: Mutated adeno-associated virus VP3 protein

<400> SEQUENCE: 8

Asn Val Asp Phe Thr Val Asp Thr Asn Gly
1               5                   10
```